US009820669B2

(12) United States Patent
Bonmassar et al.

(10) Patent No.: US 9,820,669 B2
(45) Date of Patent: Nov. 21, 2017

(54) SYSTEM AND METHOD FOR ELECTRICAL IMPEDANCE SPECTROSCOPY

(71) Applicant: THE GENERAL HOSPITAL CORPORATION, Boston, MA (US)

(72) Inventors: Giorgio Bonmassar, Lexington, MA (US); Eric S. Rosenthal, Boston, MA (US); Michael H. Lev, Newton, MA (US)

(73) Assignee: The General Hospital Corporation, Boston, MA (US)

( * ) Notice: Subject to any disclaimer, the term of this patent is extended or adjusted under 35 U.S.C. 154(b) by 318 days.

(21) Appl. No.: 14/420,148

(22) PCT Filed: Aug. 7, 2013

(86) PCT No.: PCT/US2013/053959
§ 371 (c)(1),
(2) Date: Feb. 6, 2015

(87) PCT Pub. No.: WO2014/025894
PCT Pub. Date: Feb. 13, 2014

(65) Prior Publication Data
US 2015/0190070 A1    Jul. 9, 2015

Related U.S. Application Data

(60) Provisional application No. 61/680,597, filed on Aug. 7, 2012, provisional application No. 61/680,947, filed (Continued)

(51) Int. Cl.
*A61B 5/04*      (2006.01)
*A61B 5/0478*   (2006.01)
(Continued)

(52) U.S. Cl.
CPC ........ *A61B 5/0478* (2013.01); *A61B 5/04012* (2013.01); *A61B 5/053* (2013.01);
(Continued)

(58) Field of Classification Search
USPC ........................................... 600/383
See application file for complete search history.

(56) References Cited

U.S. PATENT DOCUMENTS

2006/0125475 A1*  6/2006  Sodickson .......... A61B 5/0536
                                                                324/300

OTHER PUBLICATIONS

Bonmassar, Giorgio, Maria Ida Iacono, and Michael H. Lev. "Dual energy pulses for electrical impedance spectroscopy with the stochastic Gabor function." Engineering in Medicine and Biology Society (EMBC), 2012 Annual International Conference of the IEEE. IEEE, 2012.*
(Continued)

*Primary Examiner* — Christian Jang
*Assistant Examiner* — Mitchell E Alter
(74) *Attorney, Agent, or Firm* — Quarles & Brady LLP

(57) ABSTRACT

Systems and methods for determining brain health of a subject include or employ an electrical stimulator configured to apply a current to at least one pair of electrodes, and the electrodes are positioned on a skull of the subject to apply the current and to receive brain activity of the subject. The electrical stimulator is configured to apply a current having a waveform according to a Stochastic Gabor Function (SGF). A signal processor is configured to record the brain activity of the subject in the form of spectral electrical impedance data, and a computer system having non-transient computer readable media is programmed and configured to process the spectral electrical impedance data and indicate an impedance change within the brain of the subject.

14 Claims, 11 Drawing Sheets

Related U.S. Application Data on Aug. 8, 2012, provisional application No. 61/693,299, filed on Aug. 26, 2012, provisional application No. 61/782,031, filed on Mar. 14, 2013.

(51) Int. Cl.
*A61B 5/053* (2006.01)
*A61B 5/00* (2006.01)

(52) U.S. Cl.
CPC .......... *A61B 5/6814* (2013.01); *A61B 5/7217* (2013.01); *A61B 2562/0214* (2013.01); *A61B 2562/04* (2013.01)

(56) References Cited

OTHER PUBLICATIONS

Bonmassar, Giorgio. "The Stochastic Gabor Function Enhances Bandwidth in Finite-Difference-Time Domain S Parameter Estimation." IEEE Transactions on Microwave Theory and Techniques 55.4 (2007): 601-606.*

International Search Report and Written Opinion under dated Nov. 14, 2013 in connection with PCT/US2013/053959.

Bonmassar Giorgio et al On the Measurement of Electrical Impedance Spectroscopy (EIS) of the Human Head Int. J. Bioelectromagn, Jan. 1, 2010; 12(1):32-46.

Lugo Eduardo et al. Ubiquitous Crossmodal Stochastic Resonance in Humans: Auditory Noise Facilitates Tactile, Visual and Proprioceptive Sensations. PLoS ONE, Aug. 2008, vol. 3, Issue 8, p. 1-16.

Gabriel C. et al The Dielectric properties of biological tissues: I. Literature survey, Phys. Med. Biol. 41 (1996), 2231-2249, p. 2231.

* cited by examiner

SYSTEM AND METHOD FOR ELECTRICAL IMPEDANCE SPECTROSCOPY

CROSS-REFERENCE TO RELATED APPLICATIONS

This application is a 371 application of PCT/US2013/053959 filed Aug. 7, 2013 which claims the benefit of, U.S. Provisional Patent Application Ser. No. 61/680,597, filed on Aug. 7, 2012, 61/680,947, filed on Aug. 8, 2012, 61/693,299, filed on Aug. 26, 2012, and 61/782,031, filed on Mar. 14, 2013, all of which are incorporated herein by reference in their entirety and for all purposes.

STATEMENT REGARDING FEDERALLY SPONSORED RESEARCH

This invention was made with government support under 5U54EB007954-04, sub-contract 005213, awarded by the National Institute of Biomedical Imaging and Bioengineering of the National Institutes of Health. The government has certain rights in the invention.

BACKGROUND OF THE INVENTION

The present disclosure generally relates to systems and methods employing electrical impedance spectroscopy (EIS) for detecting, characterizing, and monitoring brain injuries and, more particularly, to systems and methods employing the Stochastic Gabor Function (SGF) and dual energy pulses for portably conducting EIS to detect, characterize, and monitor intracranial hemorrhage (ICH), stroke and other forms of traumatic brain injury (TBI). By way of example, one method includes probing using two sequential SGF pulses with two different principal energies, which can more sensitively assess deep brain tissue impedance than current, single pulse paradigms.

Intracranial hemorrhage, stroke, and traumatic brain injury are major public health problems. Computed Tomography (CT) and Magnetic Resonance Imaging (MRI) are currently the first line modalities for the evaluation of acute brain injury, including hemorrhage and stroke, but are limited in their ambulance, battlefield, and intensive care unit (ICU) availability. On the other hand, Electrical Impedance Spectroscopy (EIS) devices are portable, noninvasive devices that can provide accurate point-of-care detection, rapid triage, and serial monitoring of intracranial pathology—effectively an "EKG for the brain". For example, such a monitor need not be capable of detailed imaging, but need only alert caregivers of an event in progress, so triage to CT or MRI could be performed.

Traumatic brain injury (TBI) is the leading cause of death among individuals less than 45 years of age, affecting over 7 million people per year (over 10% of whom are hospitalized), and resulting in over 100,000 long-term disabilities and 50,000 pre-hospital admission deaths, costing approximately $50 billion dollars per year. Every 15 seconds someone suffers traumatic brain injury, and in children it accounts for more than all other causes of death combined. Causes of TBI in the United States include motor vehicle accidents (MVA, 45%), falls (20%), sports (15%), and assaults (15%).

Furthermore, with increasing use of improvised explosive devices (IEDs), blast-related concussive injury has become common. Blast waves can cause subdural hematoma, stroke, contusion, white matter hemorrhagic shear injury ("HSI," typically detectable only with specialized susceptibility weighted MRI sequences), and diffuse axonal injury ("DAI," similarly only detectable acutely with specialized diffusion weighted MRI sequences). Moreover, even the most advanced current generation MRI pulse sequences, such as diffusion tensor imaging (DTI), magnetization transfer imaging (MT), and MR spectroscopy (MRS), are incapable of detecting the subtle histological changes (for example, micro-edema and cytoarchitectural axonal disruption) associated with acute mild to moderate traumatic brain injury on an individual patient basis.

Prompt evaluation for symptoms of concussion is of high importance. DAI and HSI remain timely and vexing concerns also exist in high school, college, and professional sports (NFL, NHL, boxing). Even when portable CT scanners are available, they remain a limited resource with undependable technical support and few contingency options for equipment breakdown, cannot be used for continuous monitoring, and cannot be deployed by corpsmen in the field for emergent triage of individuals with—otherwise unapparent—subdural and epidural hematomas. A portable EIS device could therefore be of value not only in military and humanitarian assistance missions, but also more broadly in ambulances and intensive care units (ICU's) everywhere.

Stroke affects over 750,000 patients a year in the US, with the annual incidence expected to rise to 1,000,000 by 2050. The majority of strokes are ischemic (approximately 85 percent), caused by thromboembolism; the remainder are hemorrhagic. Both hemorrhagic and ischemic infarction can occur in the setting of trauma. Distinguishing between these is critical, as their prognosis, treatment, and management differ considerably. This distinction is especially important immediately following stroke onset because intracranial hemorrhage is a contraindication to thrombolytic therapy.

"Time is brain" is a well-established principle of stroke care. Early detection of infarction, and the distinction between hemorrhagic and bland ischemic change, is critical for appropriate management. For patients being evaluated for stroke, early diagnosis has a dramatic effect on the effectiveness of treatment. In patients undergoing cardiac catheterization, carotid endarterectomy, and other common endovascular procedures for which stroke is a complication, early detection would allow effective intervention and additional prevention. Further still, early detection of stroke and its complications could result not only in improved clinical outcomes (for example, stroke negatively effects more women per year than does breast cancer), but also in massive savings in rehabilitation costs, lost productivity, and other economic measures. In 2003, an estimated $57.9 billion was spent on stroke care.

When a patient is treated for ischemic stroke using thrombolytic therapy, when monitoring a hemorrhagic stroke in a neurological intensive care unit (NICU), or when monitoring patients undergoing vascular invasive procedures, detection of new or recurrent bleeding or infarct growth is crucial to patient care.

Monitoring by serial clinical neurological exam is difficult or infeasible in intubated, sedated patients, is nonspecific, difficult to quantify, and has relatively poor reproducibility. In the NICU, bedside clinical assessment using the NIH stroke scale score is the cornerstone of periodic monitoring. As expected of any clinical scale, NIHSS has significant limitations. When clinical assessment raises high enough suspicion of worsening of the intracranial lesion, the patient is transported to CT. Transportation of critically ill patients is a huge challenge; moreover, radiation exposure is a growing concern.

As discussed above, both diagnosis and follow-up of intracranial injury typically involve CT or MRI. Both of these modalities require large and expensive machines, even with limited-use "portable" CT. Moreover, CT scanning exposes patients to ionizing radiation. MRI scanning generates strong electromagnetic fields, which make it unsuitable for many patients, and MRI is incompatible with the majority of metallic and electronic hardware. Thus, it is prohibitively expensive and infeasible to continually monitor a patient in an intensive care unit using CT or MRI.

Other options for sensitive real-time monitoring of intracranial injury also have significant shortcomings. For example, invasive intracranial pressure (ICP) monitors, such as "bolts" or ventricular catheters, detect only the most catastrophic changes after ischemic stroke and do not provide information as to whether brain lesions have undergone hemorrhagic transformation. Invasive tools are also unappealing because they require invasive craniotomy and, in addition to the obvious surgical risks, carry risks of infection in this era of super-resistant bacteria (such MRSA and VRE). Even more importantly, they do not provide information regarding spatial localization. Hence, in most ICUs, ICP monitoring is currently limited to only the highest risk patients.

Non-invasive ultrasound technology (that is, transcranial doppler) permits more frequent, intermittent monitoring of a single, somewhat limited parameter: middle cerebral artery velocity. However, such a method is relatively inaccurate, requires a high level of operator expertise, measures only one vessel location at a time, is logistically difficult to implement, and thus impractical.

Near infrared spectroscopy (NIRS, that is, "optical imaging") and related optoacoustic technology (which analyzes the ultrasound signal directly transmitted from oxy- and deoxy-hemoglobin exposed to oscillating near infrared frequencies of laser light at the skin surface) have some potential as a means of battlefield detection of subdural and epidural hematomas. However, these methods are limited in both their depth of skull penetration (typically on the order of millimeters) and their extent of lateral coverage (a few square centimeters, depending on the probe array size). Moreover and like conventional ultrasound, NIRS and optoacoustic technology require handheld probes for data acquisition. As such, these methods may potentially introduce greater user-dependent variability than other methods.

Electroencephalography (EEG), which relies on non-invasive measurement of voltages produced by neuronal activity across the skull head, in principle could provide continuous monitoring. However, such a method lacks sufficient sensitivity, specificity, speed, and ease of use required for out-of-hospital diagnosis of stroke or TBI. Thus, EEG is typically used primarily for seizure detection and requires highly specialized expertise to administer and interpret.

EIS presents a potential solution for the portable, accurate, point-of-care diagnosis of injured brain. EIS is a relatively inexpensive advancement of "passive" EEG recording, in which minute electrical currents are actively applied across varying electrodes (that is, rather than passively recorded). EIS relies on non-invasive measurement and modeling of the conduction of minute electrical currents through the head, across a spectrum of frequencies. Cerebrospinal fluid (CSF) and in-situ blood, composed mainly of salt water and accounting for much of the brain's volume, have baseline low resistance to current flow. One the other hand, the edema of acute stroke and the blood clot of intracranial hemorrhage cause complex, but measurable, frequency dependent impedance changes, proportional to lesion size, composition, and location.

More specifically, EIS estimates the macroscopic dielectric constants from surface voltage measurements between electrode pairs positioned on the surface of an object (for example, a patient's head) in response to an applied probe current. For example, in one application, an EIS device delivers a small, AC current (generated using a white noise scheme) through a pair of stimulation electrodes. Voltage is recorded across three or more additional sets of bilaterally symmetric electrode pairs, according to a standard 10-20 EEG montage. The transfer function between the white-noise input and the recorded voltages are estimated, and log-log plots of the calculated impedance for each electrode are plotted as a function of the frequencies, which typically range from 100 Hertz (Hz)-100 kilo-Hertz (kHz).

In theory, EIS detects and monitors brain injuries by characterizing these impedance changes. As with MRI, however, impedance changes due to hemorrhage, stroke, and other traumatic brain injuries likely vary with time-post-insult, as the quantity and molecular conformation (and hence electrical properties) of blood clot and edema evolve.

Moreover, unfortunately, spatial localization and histological characterization of these brain injuries with existing EIS devices is limited by the disproportionate surface—as opposed to deep—current flows inherent to existing prototypes. For example, with single frequency EIS systems, one can detect shallow hematomas that create low-impedance anomalies near the skull surface, but detection of deep lesions remains challenging. Given this and the intrinsic lesion variability noted above, further refinement of existing pulse delivery systems is required to optimize the ability of EIS to: (i) reliably distinguish hemorrhagic from non-hemorrhagic injury; (ii) provide accurate anatomic localization; and (iii) sensitively assess lesion size.

From the above, it should be apparent that there is a need for inexpensive, rapid, easy-to-use, rugged, portable, non-invasive systems and methods capable of detecting, monitoring, and characterizing the bleeding or rebleeding associated with intracranial hemorrhage (ICH), the acute (cytotoxic) and subacute (vasogenic) edema associated with stroke, and the other pathological tissue changes associated with traumatic brain injury.

SUMMARY OF THE INVENTION

The present invention generally provides systems and methods for portably providing rapid, affordable point-of-care detection, assessment, and monitoring of brain injuries. These systems and methods include an improvement of electrical impedance spectroscopy (EIS) that employs the Stochastic Gabor Function (SGF) as an EIS stimulus current shape, either as a single pulse or dual pulses. For example, an optimized EIS stimulus paradigm based on dual energy pulses using the SGF can more sensitively assess deep brain tissue impedance than other single pulse EIS paradigms. The substantially increased range of depth penetration facilitated by subtraction of dual energy SGF pulses can also result in greater sensitivity and specificity for distinguishing hemorrhagic from non-hemorrhagic brain injury, and greater accuracy for the anatomic localization and size assessment of intracranial lesions. The present systems and methods may be provided as portable and noninvasive devices that may be employed in ambulance, battlefield, and intensive care unit settings.

In one aspect the present invention provides a system for monitoring the brain of a subject. The system includes an electrical stimulator configured to apply a current to at least one pair of electrodes. The electrodes are positioned on a skull of the subject to apply the current and to receive brain activity of the subject. The electrical stimulator is configured to apply a current having a waveform according to a Stochastic Gabor Function (SGF). The system also includes a signal processor configured to record the brain activity of the subject in the form of spectral electrical impedance data, and a computer system having non-transient computer readable media programmed and configured to process the spectral electrical impedance data and indicate an impedance change within the brain of the subject.

In another aspect, the present invention provides a method for monitoring the brain of a subject. The method includes positioning a plurality of electrodes on a skull of the subject, applying a current to at least one pair of the electrodes, the current based on a Stochastic Gabor Function (SGF), and measuring brain activity of the subject in the form of spectral electrical impedance data and storing the data within a non-transient computer readable media. The method also includes processing, using a computer system, the data so as to obtain an indication of an impedance change within the brain of the subject.

In yet another aspect, the present invention includes a system for analyzing a brain of a subject. The system includes a plurality of electrodes configured to be coupled to the subject to deliver excitation pulses to a brain of the subject and receive electrical information from the brain of the subject. The system also includes a controller operatively connected to the plurality of electrodes. The controller is configured to: (a) utilize a Stochastic Gabor Function to control delivery of the excitation pulses by the plurality of electrodes to the brain of the subject; (b) determine electrical information received by the plurality of electrodes from the brain of the subject in response to the excitation pulses to determine spectral electrical impedance information; and (c) generate a report indicating a status of the brain of the subject based on the spectral electrical impedance information.

The foregoing and other objects and advantages of the invention will appear in the detailed description that follows. In the description, reference is made to the accompanying drawings that illustrate a preferred configuration of the invention.

BRIEF DESCRIPTION OF THE DRAWINGS

The present invention will hereafter be described with reference to the accompanying drawings, wherein like reference numerals denote like elements, and.

DETAILED DESCRIPTION OF THE INVENTION

The present invention provides systems and methods that include an improvement of electrical impedance spectroscopy (EIS) that employs the Stochastic Gabor Function (SGF) as an EIS stimulus current shape. More specifically, the SGF is an excitation waveform that, in the present case, creates excitation pulses during EIS of the brain. The SGF is a uniformly distributed noise, modulated by a Gaussian envelop, with a wide frequency spectrum representation regardless of the stimuli energy, and is least compact in the sample frequency phase plane. The SGF facilitate both shallow and deeper tissue penetration, a capability that not is achieved with conventional stimulus paradigms. In addition, as further described below, an advantage of SGF pulse delivery is the potential for "dual energy" subtraction imaging that can more sensitively assess deep brain tissue impedance than current single pulse paradigms.

EIS is maximally sensitive to impedance changes at the electrode-skin interface and is relatively less sensitive to deep brain parenchymal changes due to the limited penetration of the probe current. Tissues in the human head are dispersive and the EIS current density distribution depends on the sensing stimulation frequency. Tissues such as bone and CSF tend to divert currents entering the brain because their conductivities are very different from that of brain parenchyma. Different approaches have been proposed to measure EIS signal. Because a sinusoidal sensing pulse at a single, individual frequency cannot fully characterize small differences in dielectric constant between different tissues, alternative pulse generation schemes have been developed, mainly using multi-tone or frequency sweep methods. One existing method uses a 0-50 kilo-Hertz (kHz) "white noise" stimulation pulse, currently being used for studies of patients with acute and subacute brain injury.

Because frequency difference imaging can further improve sensitivity and specificity for the detection of deep intracranial lesions, some implementations of the present invention provide a probe current design based on the concept of dual energy. As further described below, an optimized EIS stimulus paradigm based on dual energy pulses using the SGF can more sensitively assess deep brain tissue impedance than other single pulse EIS paradigms, including the existing, "white noise" stimulus excitation pulse method. The substantially increased range of depth penetration facilitated by subtraction of dual energy SGF pulses can also result in greater sensitivity and specificity for distinguishing hemorrhagic from non-hemorrhagic brain injury, and greater accuracy for the anatomic localization and size assessment of intracranial lesions. The SGF is advantageous as a basis for dual energy pulse stimulus because it reaps the benefits of a very wide frequency bandwidth, while retaining a non-narrow pulsed envelope in time.

Figure 1:
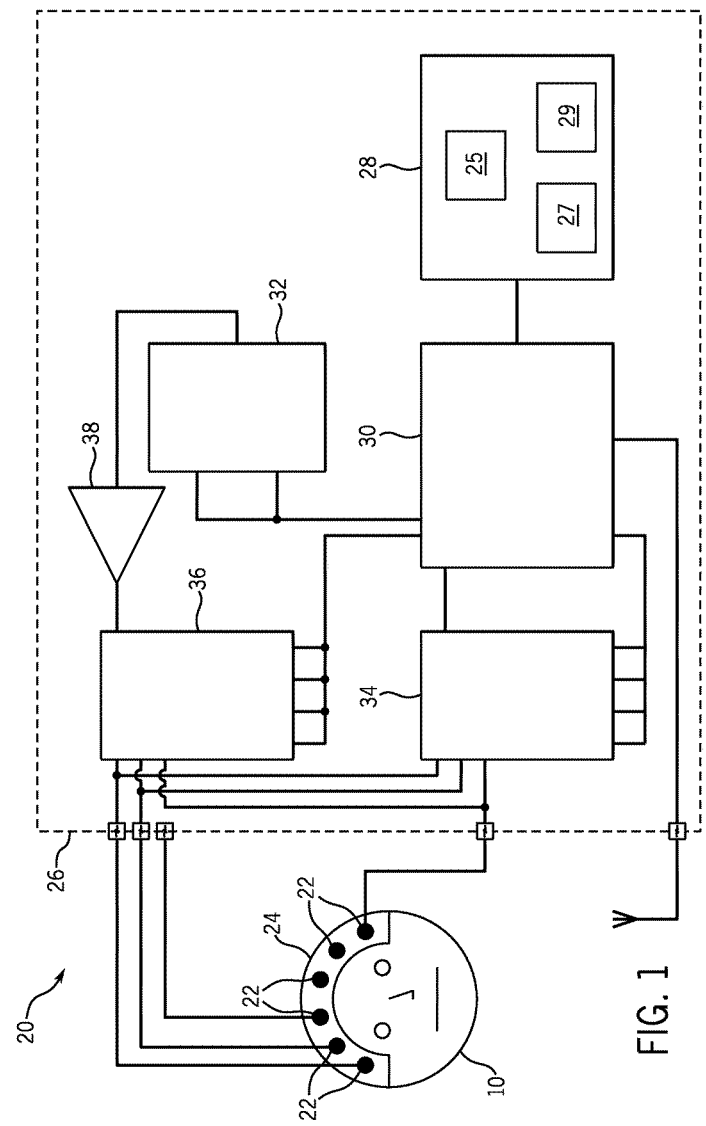
FIG. 1 is a schematic view of an improved EIS system according to the present invention.
Figure 2:
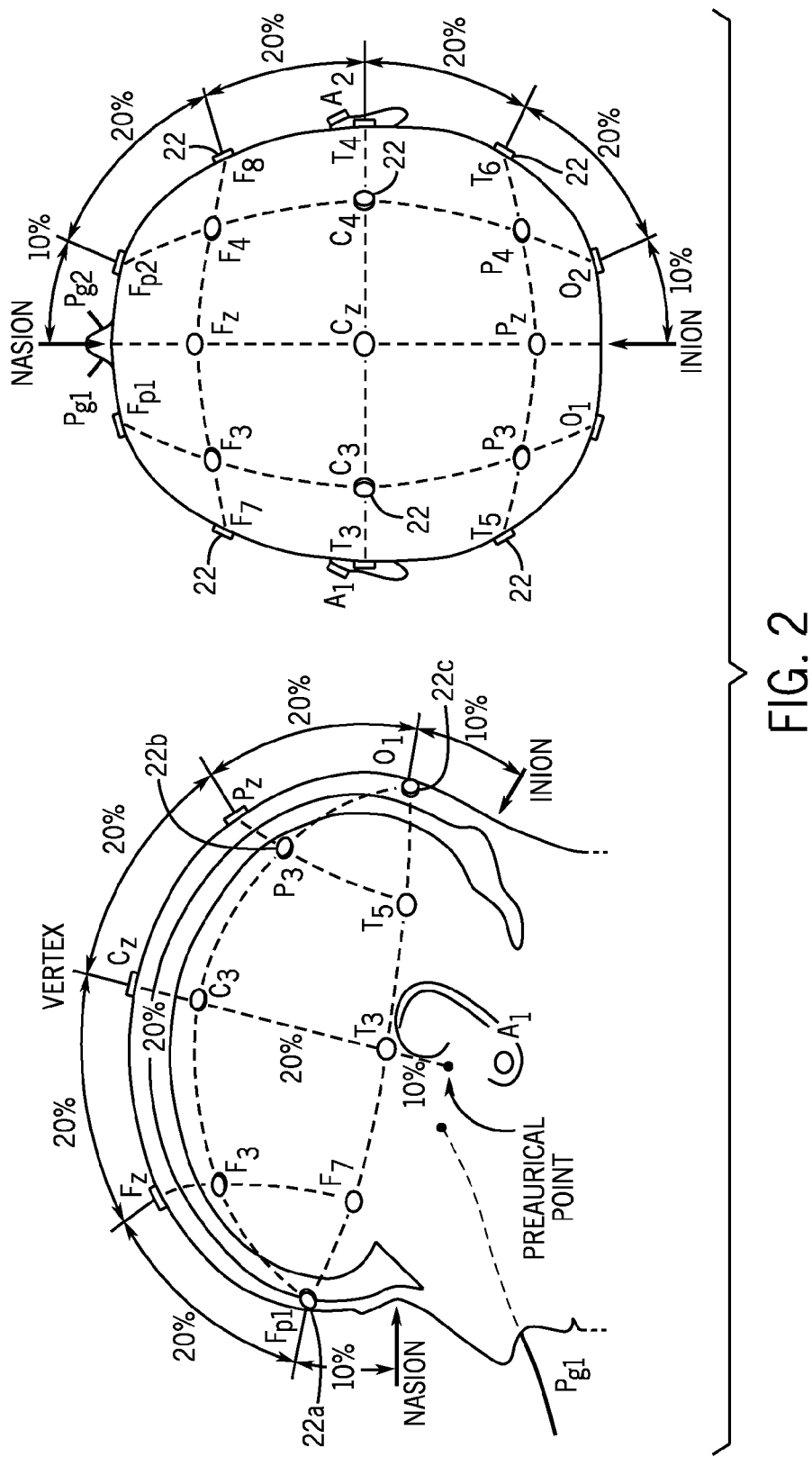
FIG. 2 illustrates an example electrode configuration for use with the improved EIS system of FIG. 1.

An exemplary EIS system 20 according to the present invention is shown in FIG. 1. The EIS system 20 includes a plurality of electrodes 22 such as those that are commonly associated with EEG. The electrodes 22 are supported proximate a patient's head or skull 10 by a cap 24. Alternatively, other electrode support structures, such as headbands or the like, may be used. In some implementations, the EIS system 20 can include at least a single pair, 4 pairs, 6 pairs, or 8 pairs of electrodes. One or more of the electrodes 22 act as transmitter electrodes (for example, at least one pair of electrodes 22), and these electrodes are directed by an operatively connected controller 26 to transmit one or more SGF-created excitation pulses to the patient's head 10 (in other words, current having a waveform according to the SGF). One or more of the other electrodes 22 act as receiver electrodes and receive the excitation pulses via the patient's head 10. The controller 26 operatively connects to the receiver electrodes 22 and analyzes the received pulses (that is, brain activity of the subject 10 in the form of spectral electrical impedance data) to determine impedance characteristics of the patient's head 10. By way of example, FIG. 2 illustrates an example EIS electrode montage, including a plurality of electrodes 22 about a patient's head 10 in accordance with the traditional 10-20 system. As shown in FIG. 2, the electrodes 22 can include a stimulation electrode 22a, a reference electrode 22b, and a stimulation ground electrode 22c.

The controller 26 includes a computer system 28 (for example, a commercially available desktop or laptop PC, a tablet computer, a smartphone, or the like) for initiating EIS processes and analyzing result data to determine impedance characteristics of the patient's head 10. The computer system 28 includes a user interface 25, a processor 27, and non-transient computer readable media 29. The computer system 28, via the processor 27, is configured to record brain activity of the subject 10, for example, in the form of spectral electrical impedance data, and store such data in the non-transient computer readable media 29. Furthermore, the computer system 28 is programmed and configured to process the data and indicate an impedance change within the brain of the subject 10, as further described below. The computer system 28 operatively connects to an analog-to-digital converter (ADC) 30, which in turn operatively connects to a pulse generator 32 (or electrical stimulator) that creates excitation pulses based on the SGF. The ADC 30 operatively connects to a first multiplexer 34, and the pulse generator 32 operatively connects to a second multiplexer 36 via an amplifier 38. The first and second multiplexers 34 and 36 operatively connect to the electrodes 22. The EIS system 20, as described above, can be both non-invasive and portable. In addition, in some implementations, the EIS system 20 can be structured or configured similar to that described in United States Patent Publication No. 2012/0150059, the entire contents of which is incorporated herein by reference.

Figure 3:
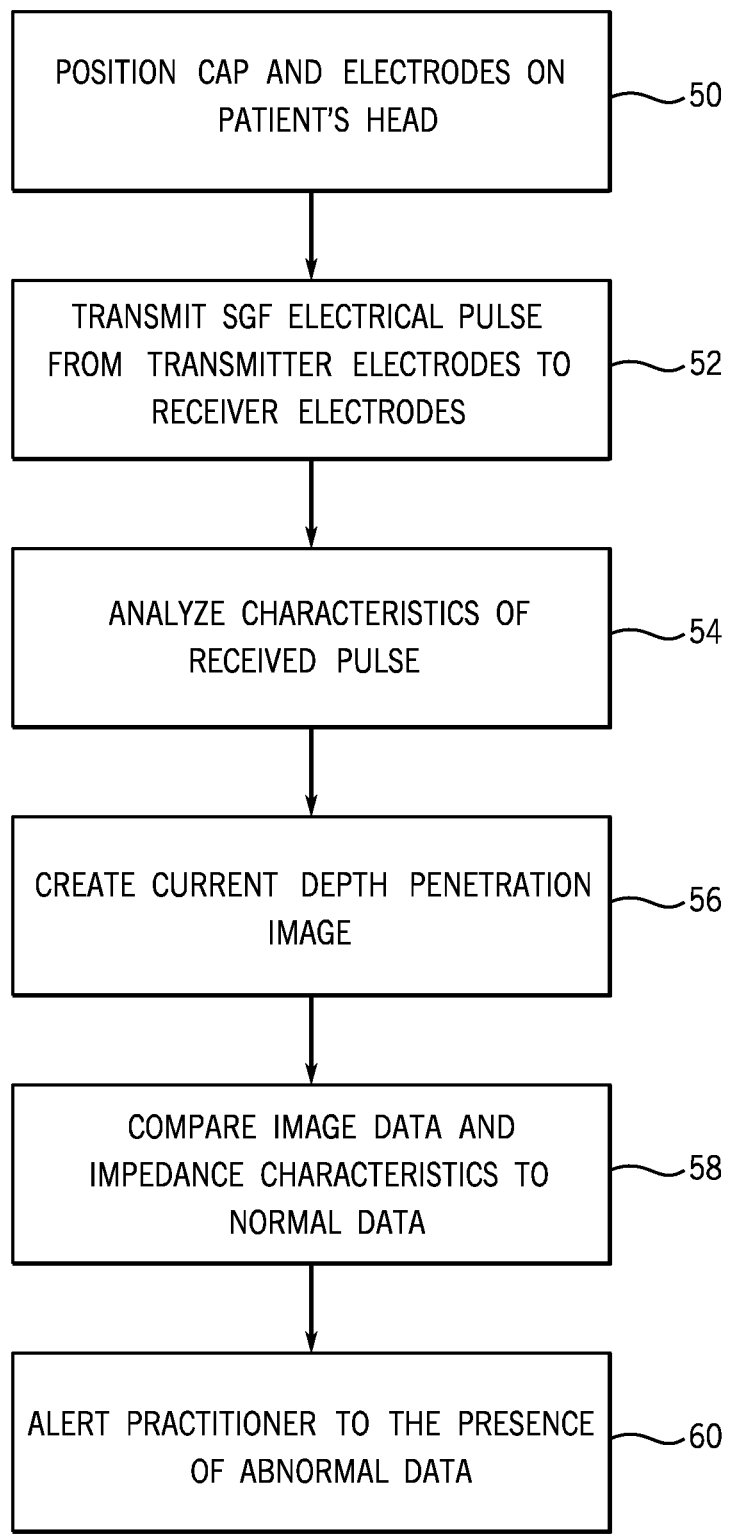
FIG. 3 illustrates an EIS method according to the present invention.
Figure 10A:
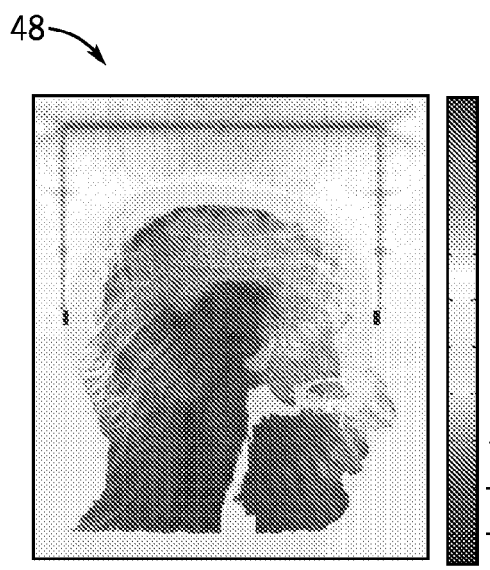
FIG. 10A is a simulation plot of the electric field in and around a realistic head model when applying an exemplary high-energy SGF pulse.

Turning now to FIG. 3, an exemplary method according to the present invention proceeds as follows. At process block 50, the method begins by placing the cap 24 and the electrodes 22 on the patient's head 10. Next, the controller 26 directs the transmitter electrodes 22 to transmit an SGF-created pulse (of current) to the receiver electrodes 22 via the patient's head 10 at process block 52. In some implementations, for example, the SGF-created pulse can be in the range of about 10,000 kilo-Hertz (kHz) to about 100,000 kHz. In other implementations, the SGF-created pulse can be in the range of about 30,000 kHz to about 500,000 kHz. At process block 54, the controller 26 analyzes characteristics of the received pulse. Based on these characteristics, the controller 26 creates a current depth penetration image (for example, as shown in FIG. 10A) representing electric field and impedance characteristics of the patient's head 10 at process block 56.

At process block 58, the controller 26 automatically compares the depth penetration image data and impedance characteristics to previously obtained or previously loaded "normal" data (that is, data corresponding to healthy brain tissue) to detect abnormal data (that is, data indicative of brain injury). By way of example, electrical properties of normal brain tissue, such as impedance, vary as a function frequency (based on the dielectric constants of such tissue). Output impedance measurements as a function of frequency illustrate characteristic curves that differ in normal tissue versus pathological tissue. More specifically, edema and hemorrhage, which can both accompany stroke, focally alter the electrical resistance of brain tissue. The impedance of tissue after ischemic stroke is increased due to reduced extracellular fluid or cell swelling. In contrast, the impedance of tissue after hemorrhagic stroke or chronic stroke is reduced because the conductivity of blood and CSF are about three times greater than that of the surrounding brain tissue. Thus, abnormal data is characterized by notable changes in impedance from the "normal" data and such abnormal data can be an indication of stroke. Such notable changes may be determined by analyzing curve coefficients of recorded data to curve coefficients of previously loaded normal data.

If abnormal data is detected at process block 58, the controller 26 alerts a practitioner (such as a surgeon, medic, first responder, or the like) to the presence of the abnormal data (for example, via an audible indication, a visual message provided on a display of a user interface, or the like) at process block 60. In other exemplary embodiments, the depth penetration image may instead be analyzed by a practitioner (such as a surgeon, medic, first responder, or the like) to determine the patient's brain health. In other exemplary embodiments, the controller 26 may analyze the data as described above without creating or presenting a depth penetration image to the practitioner. Instead, the controller 26 could simply alert the practitioner to the presence of abnormal data. In some implementations, the controller 26 may also characterize the abnormal data, for example, by distinguishing between hemorrhagic versus ischemic abnormal data and alert the practitioner accordingly.

Figure 4:
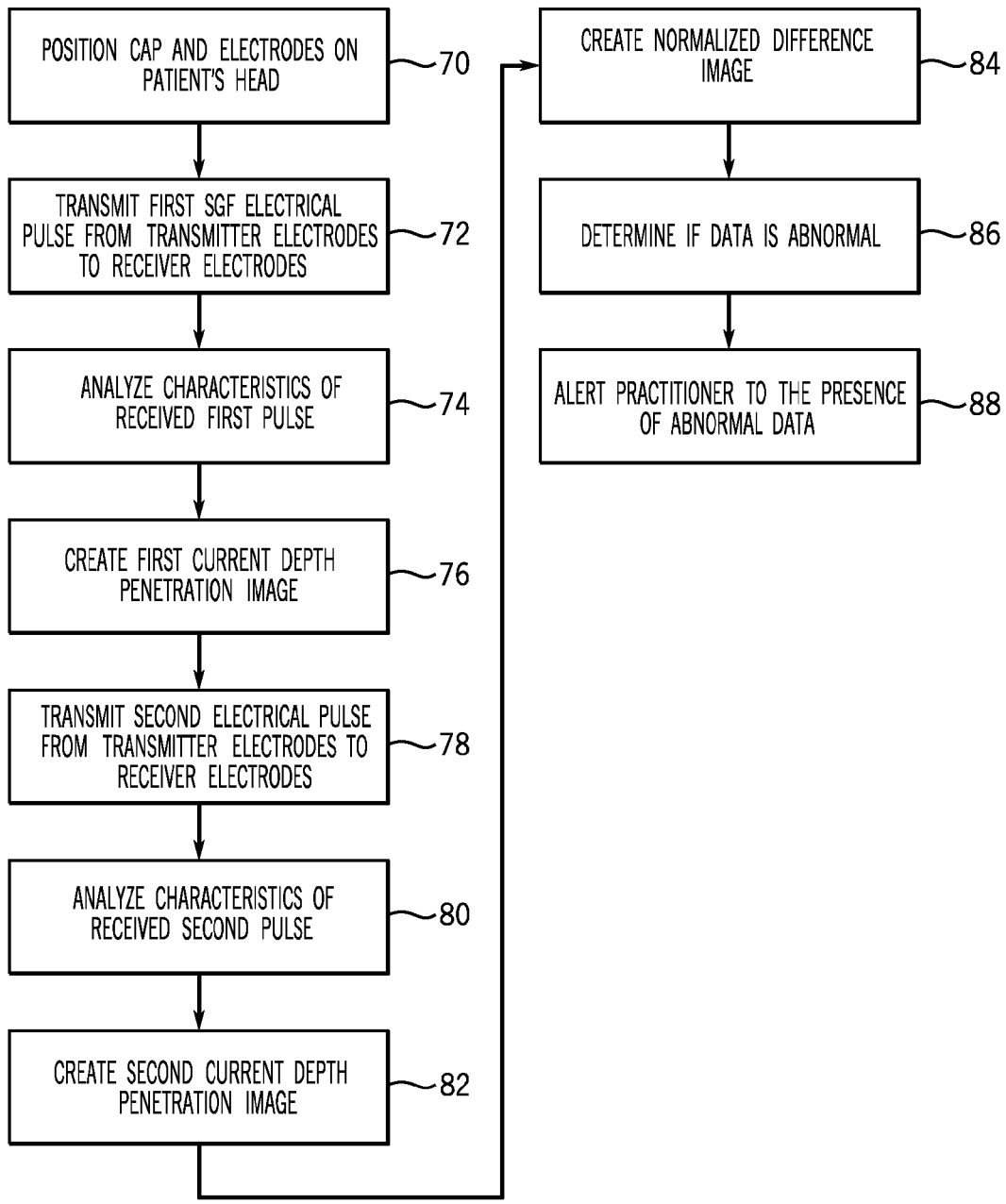
FIG. 4 illustrates another EIS method according to the present invention.
Figure 10B:
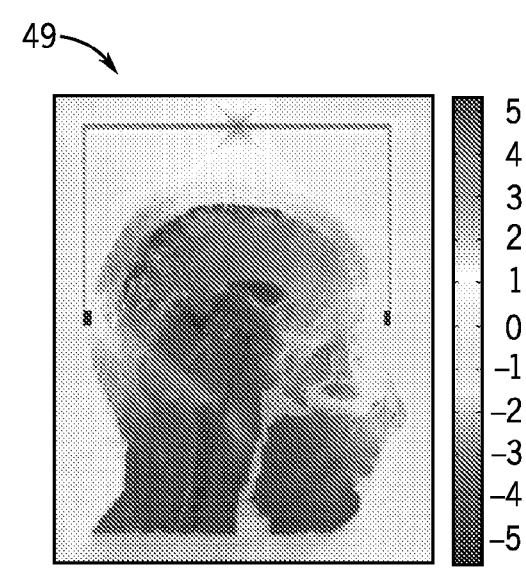
FIG. 10B is a simulation plot of the electric field in and around the realistic head model when applying an exemplary low-energy SGF pulse.

Turning to FIG. 4, an exemplary "dual energy" or "subtraction imaging" method according to the present invention begins in the same manner as the previous method. That is, at process block 70, the method begins by placing the cap 24 and the electrodes 22 on the patient's head 10. Next, the controller 26 directs the transmitter electrodes 22 to transmit a first SGF-created excitation pulse to the receiver electrodes 22 via the patient's head 10 at process block 72. At process block 74, the controller 26 analyzes characteristics of the received first pulse. Based on these characteristics, the controller 26 creates a first current depth penetration image (for example, as shown in FIG. 10A) at process block 76. Next, the controller 26 directs the transmitter electrodes 22 to transmit a second excitation pulse to the receiver electrodes 22 via the patient's head 10 at process block 78. The second excitation pulse may also be created by the SGF but have a different energy magnitude than the first excitation pulse, or the second excitation pulse may be a non-SGF-created pulse (for example, a white noise-based pulse) having a different energy magnitude than the first excitation pulse. As further described below, SGFs with different energies exhibit different penetration depths within tissue (more specifically, penetration depth is proportional to frequency). In some implementations, penetrations depths may differ by greater than about 1 millimeter. At process block 80, the controller 26 analyzes characteristics of the received second pulse. Based on these characteristics, the controller 26 creates a second current depth penetration image (for example, as shown in FIG. 10B) at process block 82.

Figure 13:
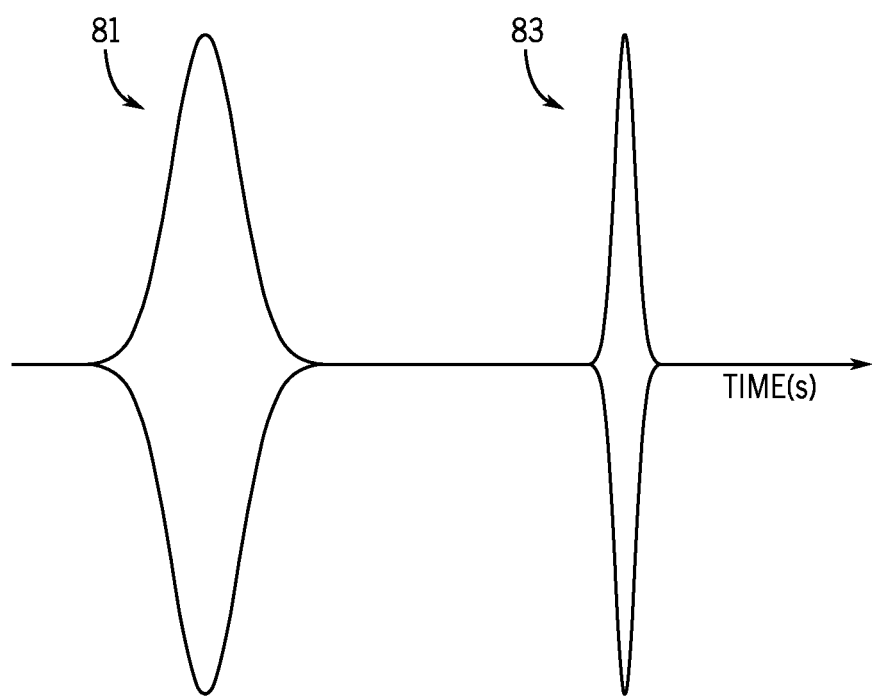
FIG. 13 illustrates an example amplitude versus time plot of dual energy pulses.

In some implementations, the two excitation pulses (from process blocks 72 and 78) may be applied as dual energy pulses 81, 83 over a time period, for example as illustrated in FIG. 13. Accordingly, process blocks 74 and 76, as well as process blocks 80 and 82 may be performed after application of the dual energy pulse at process blocks 72 and 78.

Figures 12A, 12B, 12C:
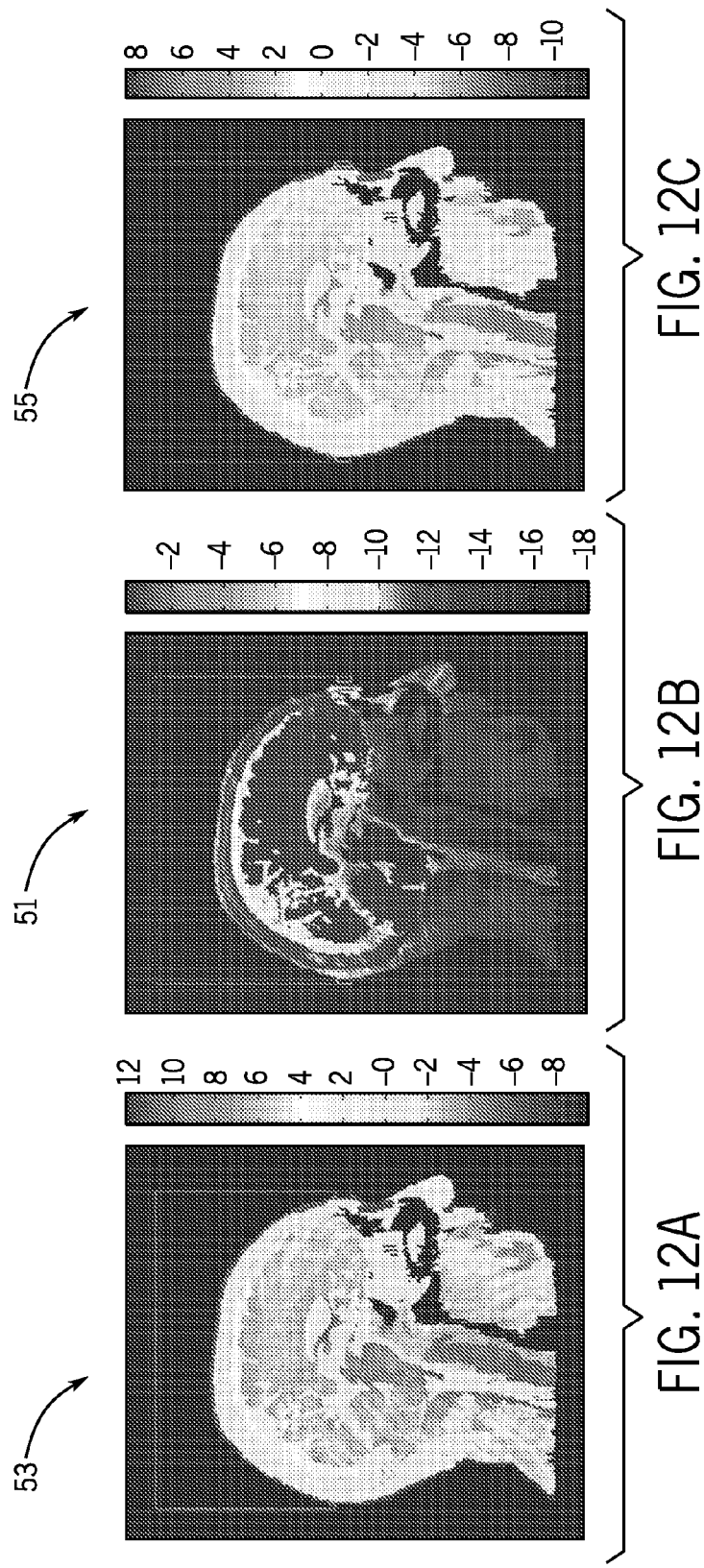
FIG. 12 illustrates simulation plots of current densities integrated over time for the high-energy SGF pulse of FIG. 10A (FIG. 12A), the low-energy SGF pulse of FIG. 10B (FIG. 12C), and a normalized difference map between the low-energy SGF pulse and the high-energy SGF pulse (FIG. 12B)

At process block 84, the controller 26 creates a normalized difference image (for example, as shown in FIG. 12B) including features from the first current penetration depth image and the second current penetration depth image. However, the normalized difference image lacks features common to both the first current penetration depth image and the second current penetration depth image. At process block 86, the controller 26 automatically determines if the normalized difference image data and the impedance characteristics are abnormal. If abnormal data is detected, the controller 26 alerts a practitioner to the presence of the abnormal data at process block 88. In some implementations, the Fourier transforms of each of the weighted SGF current stimulation pulses and the weighted synchronous responses can be individually subtracted. The resulting Fourier transformed subtracted input and output values can then be deconvolved to estimate the complex impedance as a function of frequency. The resulting impedance as a function of frequency can be analyzed for existence of abnormal data.

Accordingly, the above method of FIG. 4 utilizes two SGF pulses at different energies to achieve an optimal excitation when used in a dual energy subtraction scheme. Despite the fact that the two different SGF pulses exhibit different tissue current distributions, they still maintain the broadband sensing pulse characteristics needed to stimulate all the frequencies of interest. Furthermore, as further described below, by subtracting the response of the two pulses, EIS sensitivity decreases in regions that would otherwise receive the highest current density (such as skin, subcutaneous fat, etc.), but increases in what would otherwise be low current density regions, such as the brain parenchyma. Thus, SGF subtraction imaging allows for greater sensitivity than is currently obtainable with conventional "single" pulse EIS stimulation paradigms, and can facilitate assessment of parenchymal dielectric changes as a function of frequency. This facilitates greater sensitivity and specificity in EIS detection and characterization of acute intracranial hemorrhage, stroke, and other brain injuries by highlighting abnormalities in tissue impedances specific to such lesions.

In the following paragraphs, the SGF is defined, statistical parameters of the Gaussian, Gabor, and SGF stimuli are delineated, and dual energy example stimuli using a realistic head model for EIS application are provided.

Figure 5:
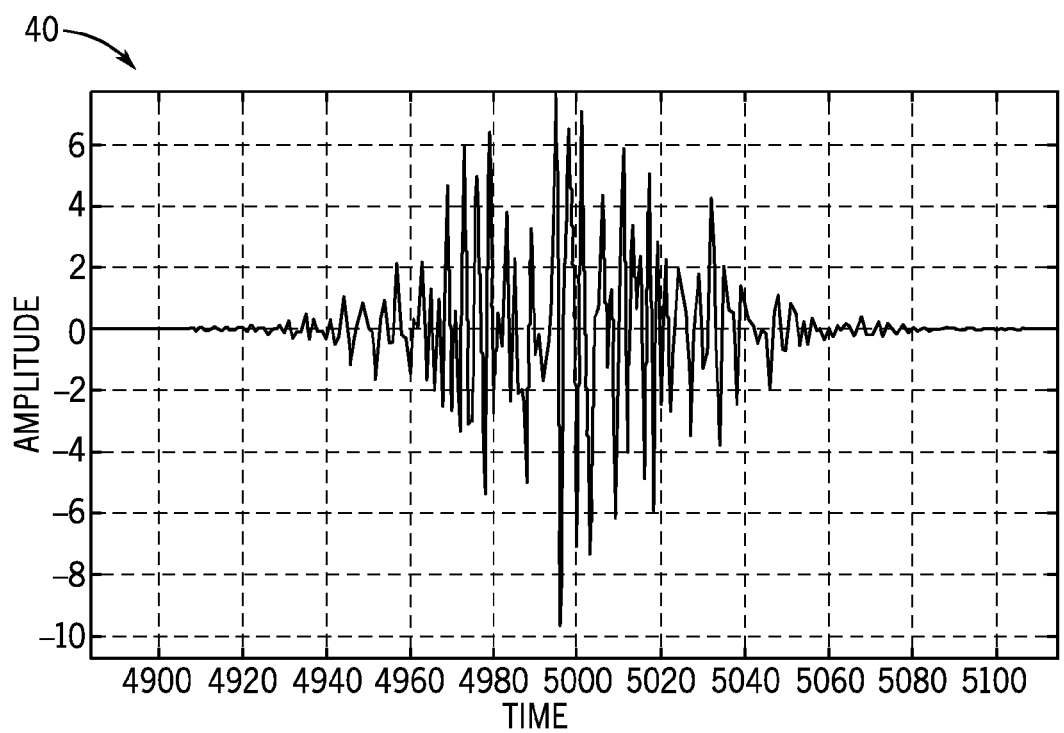
FIG. 5 is an amplitude versus time plot of the Stochastic Gabor Function (SGF)

Generally, the SGF may be considered uniformly distributed noise modulated by a Gaussian envelope. More specifically, the SGF 40 is illustrated in FIG. 5 (in an amplitude versus time plot) and is defined as:

$$\lambda_n = \xi_n g_n^\sigma, \quad (1)$$

where $n \in [1:N]$, $\xi_n$ is a random Gaussian white noise process uniformly distributed in $[-1; 1]$, and $$g_n^\sigma = \frac{\exp\left[-\frac{n^2}{2\sigma^2}\right]}{\sigma\sqrt{2\pi}}$$

is the Gaussian function. The $\xi_n$ set is valid only if the resulting SGF is zero-mean (that is, $\langle \lambda_n \rangle = 0$). The power spectral density of $$\wp_k = S_k^{\xi\xi} * |G_k^{1/\sigma}|^2 \cong C \quad (2)$$

where $k \in [1:N]$ is the frequency variable and $S_k^{\xi\xi}$ is the discrete Fourier transform, or FFT, of the autocorrelation function of the white noise process $\xi_n$; $G_k^{1/\sigma}$ is the FFT of $g_n^\sigma$. The whitening of the Gaussian in equation (1) flattens the frequency response. The short-time Fourier Transform is used to determine the sinusoidal frequency and phase content of a signal inside a time window, following the spectral changes of the signal over time. The short-time Fourier Transform of the Stochastic Gabor Function is:

$$\Gamma_{k,m} = \sum_{n=1}^{N} \lambda_n w_{n-m} \exp[-j2\pi nk] \quad (3)$$

where $m \in [1:N]$ specifies the position of the time window and $w_n$ is the time window function such that $$\sum_{n=1}^{N} |w_n|^2 = 1.$$

By selecting a Gaussian, $w_n = g_n^{\tilde{\sigma}}$, as the window function, $$\Gamma_{k,m} = \sum_{n=1}^{N} \xi_n g_n^\sigma g_{n-m}^{\tilde{\sigma}} \exp[-j2\pi nk] \quad (4)$$

and the short-time power spectral density becomes:

$$\wp_{k,m} = S_k^{\xi\xi} * |G_k^{1/\sigma} * G_k^{1/\tilde{\sigma}} \exp[j2\pi mk]|^2 \cong C g_m^{2(\sigma+\tilde{\sigma})} \quad (5)$$

Figure 6:
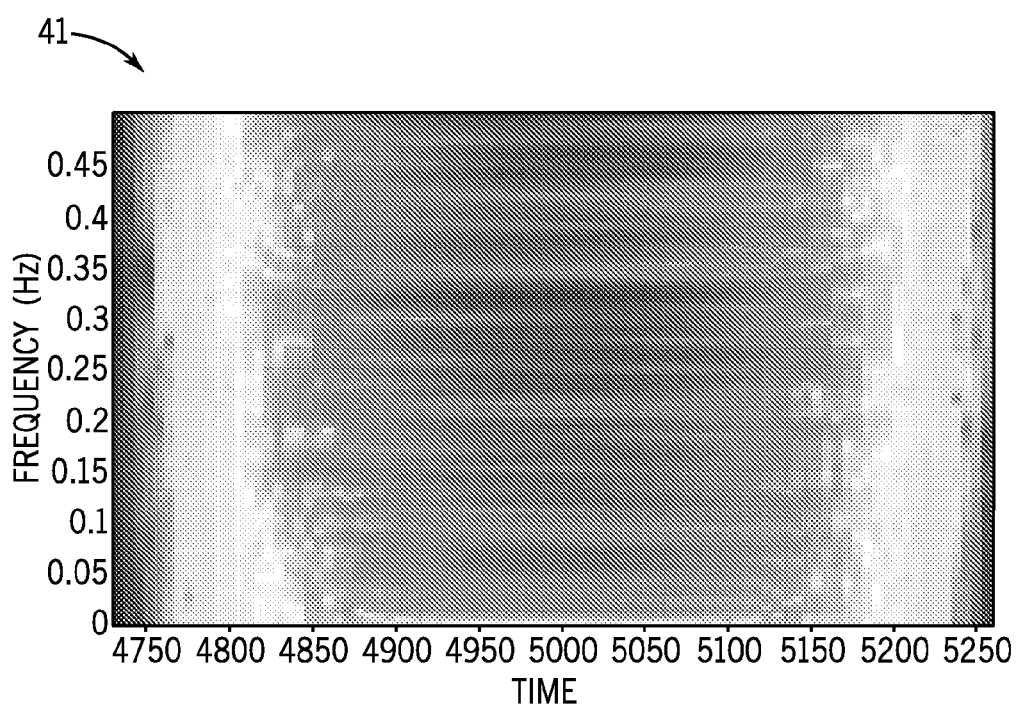
FIG. 6 is a spectrogram of a frequency representation of the Stochastic Gabor Function's Gaussian envelope in the time domain.
Figure 7:
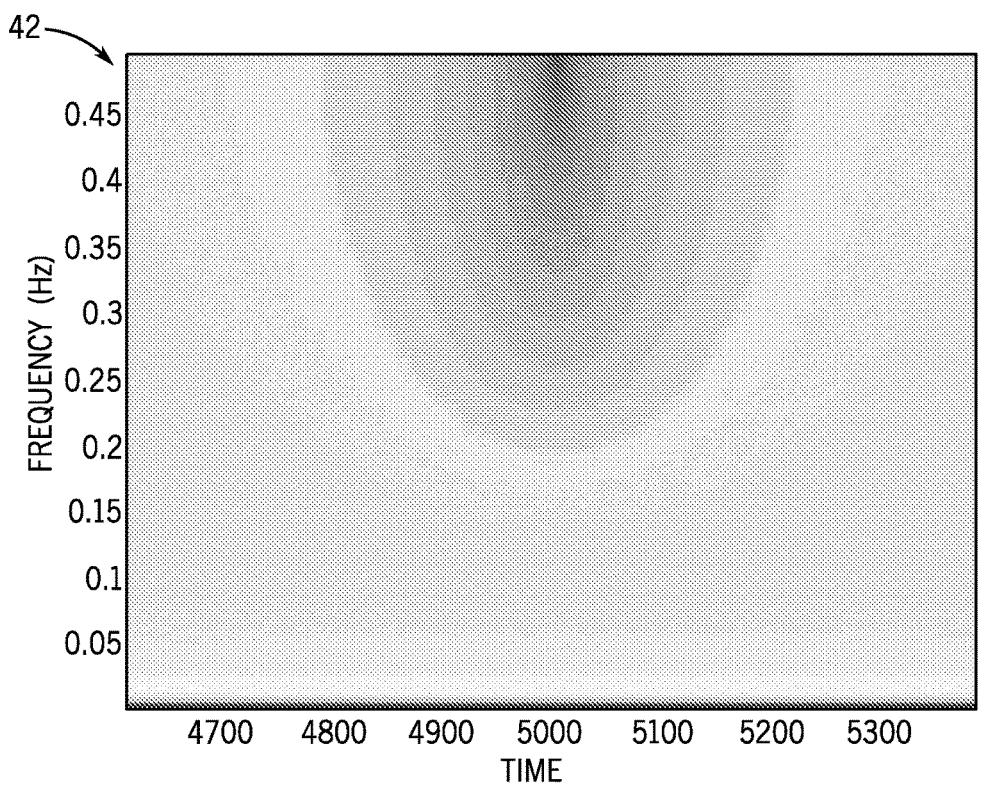
FIG. 7 is a spectrogram of a Gauss function representation of a Gaussian ($\sigma$=12.8, N=64,000)
Figure 8:
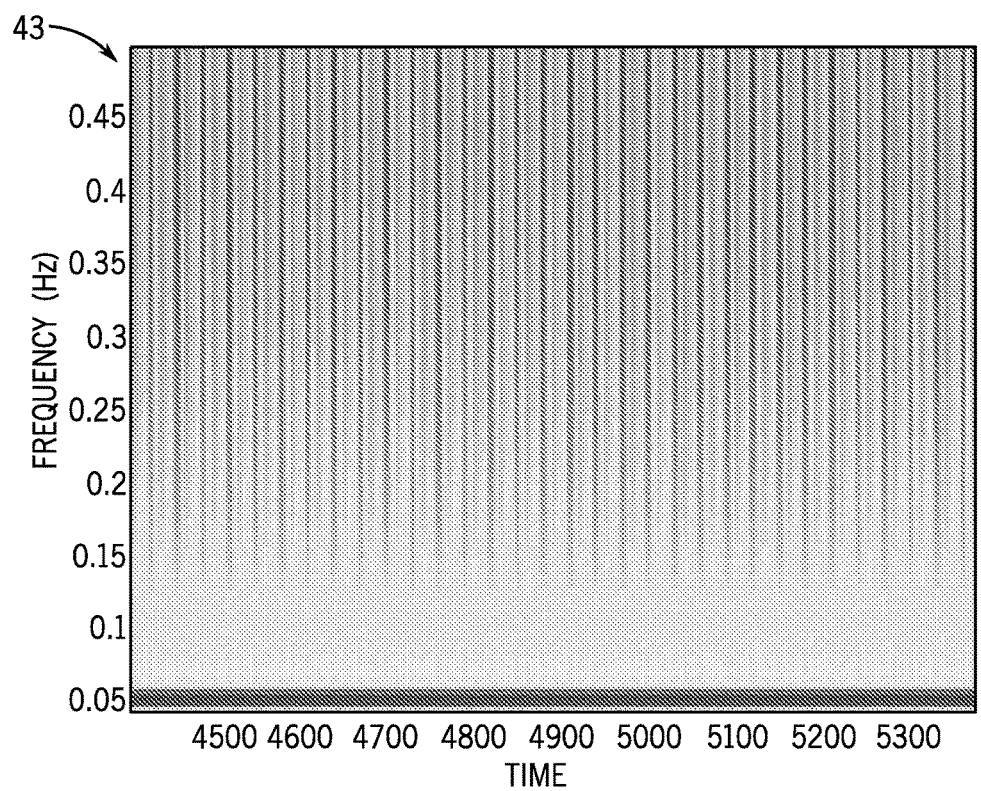
FIG. 8 is a spectrogram of the Gabor function ($\omega_0$=0.1)

The Stochastic Gabor Function is modulated by a Gaussian envelope in the time domain; its frequency representation 41 (as shown in FIG. 6) is very uniform. A Gaussian 42 (shown in FIG. 7) has a Gauss function representation in both time and frequency domains. The Gabor function 43 (shown in FIG. 8), a harmonic function with frequency $w_0$ multiplied by a Gaussian, has the same time-frequency distribution as the Gaussian but shifts in frequency by $w_0$.

One of the main advantages of the Gaussian and Gabor functions is their time-frequency localization. In the following paragraphs, the Stochastic Gabor Function is studied in terms of localization in the time domain, which can be measured by estimating the time-frequency resolution to select the value for σ, or pulse width of the Stochastic Gabor Function. A more uniform sampling in frequency corresponds to a source excitation with lower concentration in the sample frequency phase plane:

$$H(\Gamma_n) = \sum_{n=1}^{N} \|\Gamma_n\|^2 \log(\|\Gamma_n\|^2 + \varepsilon) \qquad (6)$$

where $\varepsilon$ is an arbitrarily small constant introduced for regularization. Equation (6) has a form similar to the entropy function, $E(p_i) = -p_i \log(p_i)$; however, the resulting quantity is an estimate of frequency concentration when the hermitian vector $\Gamma_n$ is transformed into a real vector using the square norm. When all frequency values of $\Gamma_n$ are constant, $H(\Gamma_n) = 0$. Conversely, $H(\Gamma_n)$ reaches maximal value when the function $\Gamma_n$ is concentrated at a single frequency point. For instance, zero frequency concentration occurs when $\lambda_n = [1\ 0\ 0\ 0]$, where $\Gamma_n = [1\ 1\ 1\ 1]$ results in $H(\Gamma_n) = 0$. High frequency concentration occurs when $\lambda_n = [1\ 1\ 1\ 1]$, in which case $\Gamma_n = [4\ 0\ 0\ 0]$ and results in $H(\Gamma_n) \cong 44.4$ (with $\varepsilon = 10^{-10}$).

Figure 9:
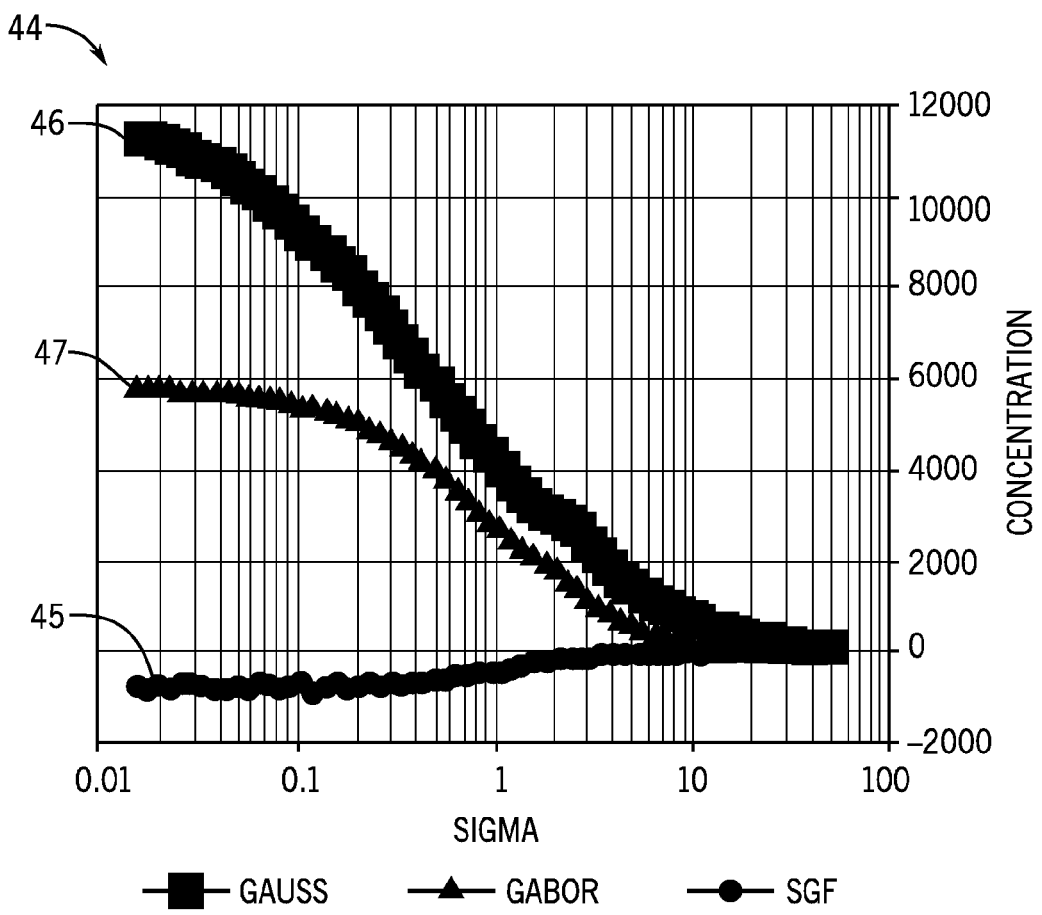
FIG. 9 is a plot of frequency concentration with N=512 and $\epsilon=10^{-10}$ of the Gaussian function (represented with diamonds), the Gabor function with $\omega=6\pi$ (represented by squares), and Stochastic Gabor Function (represented by triangles)

FIG. 9 illustrates a plot 44 of the difference in frequency concentration as a function of the pulse width σ. In the case of larger σ values, the Stochastic Gabor Function 45, which is virtually flat in frequency, exhibits much lower concentration in the sample frequency phase plane than either the Gaussian function 46 or the Gabor function 47. The Gabor is less concentrated in frequency than the Gaussian, as it is composed of two Gaussians centered at $\omega_0$ and $-\omega_0$. As the pulse width approaches zero, all functions approach $\lambda_n = \delta_n$ such that the frequency concentration also approaches zero. The concentration property allows for shorter exciting pulses and has the advantage of reducing the number of time steps needed for Finite Differences Time Domain (FDTD) convergence (see, for example, Bonmassar G (2007) The Stochastic Gabor Function Enhances Bandwidth In Finite-Difference-Time Domain s-Parameter Estimation. Microwave Theory and Techniques, IEEE Transactions on 55: 601-606, the entire contents of which are incorporated herein by reference).

The propagation of currents inside the human head can be expressed by the following set of quasi-static approximation:

$$\nabla \sigma \omega + j \omega \varepsilon_0 \varepsilon_r \omega + E \omega + E_0 \omega + J_e \omega + \omega P \omega = 0, \qquad (7)$$

with the assumptions that the induced electric field is curl free, or equivalently that skin effect and wave propagation effects can be ignored. Assuming a time harmonic Electric Field, it is known that in a lossy dispersive medium the electric energy density in a point $P \in (x_0, y_0, z_0)$ in the medium:

$$W_P \omega = \frac{1}{2} \sigma_P \omega E_0 \omega^2 \qquad (8)$$

After discretizing and introducing the SGF with an external current applied along a direction v with power spectral densities $J_{e,k} = v \wp$ in Equation 6 discretized, the local conductivity is:

$$\sigma_{P,k} = \frac{2W_{P,k}}{E_{P,k}^2} \qquad (9)$$

When applying two SGF pulses at different times and subtracting the effect of the two different local energies $W_{P,k}^A$, $W_{P,k}^B$ and electric fields $E_{P,k}^A$, $E_{P,k}^B$:

$$\sigma_{P,k} = 2\frac{W_{P,k}^A}{E_{P,k}^{A2}} - \frac{W_{P,k}^B}{E_{P,k}^{B2}} \qquad (10)$$

$\sigma_{P,k}$ is not zero since the two SGF probing function have different power spectral densities: $S_k^{\xi\xi} * |G_k^{1/s_1}|^2 \ne S_k^{\xi\xi} * |G_k^{1/s^2}|^2$, with different energies or variances ($s_1^2$ and $s_2^2$) and two different states of the white noise ergodic process ($\xi$).

FIGS. 10A-12C illustrate how the Stochastic Gabor Function can modulate the penetration depth in a realistic head model when used as a probe current pulse in EIS (such a head model is described in Makris N, Angelone L, Tulloch S, Sorg S, Kaiser J, et al. (2008) MRI-based anatomical model of the human head for specific absorption rate mapping. Med Biol Eng Comput 46: 1239-1251, the entire contents of which are incorporated herein by reference). Numerical simulations of a normal brain using this head model (using Finite Differences Time Domain, FDTD) illustrate that the depth of penetration of two different SGF pulses, with two different principal energies, varies in the lossy media of the human head. More, specifically, simulation results 48, 49 are shown in terms of the electric field in and around the head using two different values of the σ for the SGFs (shown in FIGS. 10A and 10B, respectively), which resulted in a different current density penetration profile 53, 55 between the two SGFs (shown in FIGS. 12A and 12C, respectively, with the subtraction image 51 shown in FIG. 12B). In particular, the high-energy pulse (used in FIGS. 10A and 12A) provides a significant increase of tissue penetration compared to the low-energy pulse (used in FIGS. 10B and 12C) for the magnitude of the electric field integrated over time in the same logarithmic scale. The following paragraphs describes these numerical simulations and their results in more detail.

The geometry from a previously developed, 1×1×1 mm³ resolution head model was adopted in the electromagnetic finite difference time domain (FDTD) simulations with predetermined parameters. The overall simulated geometry dimensions were 170 mm in width, 217 mm in depth, and 238 mm in height. Each tissue of the head model was modeled under the common assumption of linearity of the $\vec{E}$-field, nondispersive, isotropic medium, and heterogeneous space using a one-pole Debye-Drude model based on its histological properties. The Debye-Drude dispersion model was defined as follows:

$$\hat{\varepsilon}_d(\omega) = \varepsilon_\infty + \frac{\Delta \varepsilon}{1 + j\omega \tau_1} + \frac{\sigma_1}{j\omega \varepsilon_0}, \qquad (11)$$

where $\sigma_1$ is the static ionic conductivity, $\epsilon_\infty$ is the permittivity at field frequencies $\omega\tau \gg 1$, $\epsilon_0$ is the permittivity of free space, $\Delta\epsilon = \epsilon_s - \epsilon_\infty$ is the magnitude of the dispersion and $\epsilon_s$ is the permittivity at field frequencies $\omega\tau \ll 1$. In the model, two standard EEG electrodes with 10 mm diameter were modeled with perfect electrical conductors (PEC) and were connected through PEC wires to a current source that generated the two SGF pulses: the lower energy SGF was defined with s=128 and the higher energy with s=12.8 both with $N_s$=105. The weighted current density was defined as:

$$\vec{J}_{w,k} = w\vec{J}_k^A - (1-w)\vec{J}_k^B, \quad (12)$$

where $\vec{J}_k^A$, $\vec{J}_k^B$ are the current densities of the low and high energy SGF respectively with peak amplitude normalized to 1 amperes per meter squared (A/m²). All components are shown at 500 kHz, and were computed using the chirp transform of (such as the "czt" command in MATLAB) of the electric fields and of the current densities distribution in MATLAB. All electrical components were computed using commercially available software (XFDTD v. 7, Remcom Inc., State College, Pa.) based on the FDTD algorithm. The geometrical grid consisted of 1 mm³ uniform Yee cells. The volume of the FDTD grid including the head model and the EIS electrodes was 4,642,730 Yee cells. The total size of the geometry, including the free space around the head model, was 323×373×323 mm³. Seven perfectly matching layers were used for boundary conditions in all simulations. The timestep used to ensure FDTD Courant-Friedrich-Levy stability was 1.92 picoseconds (ps). The computation times for both SGF stimuli were 5 minutes for $N_s$=105, respectively, using an eight cores Dell Precision T7500 desktop computer with 48 gigabyte of RAM on a C2070 graphics processing unit (GPU) (Nvidia, Santa Clara, Calif., USA) with 6 GB graphics memory.

FDTD simulations were performed to study the sensitivity or the current density of the proposed SGF dual energy pulse in deep brain structures. FIGS. 10A and 10B illustrate the distribution of the electric field magnitude $|\vec{E}|$ in logarithmic scale (decibels (dB)) relative to 1 V/m) generated by the two different Stochastic Gabor Functions, respectively in a realistic head model when used as a probe current pulse through the two EIS electrodes. The results are shown at 500 kHz in and around the head using two different values of the energy or variance $s^2$ for the SGFs. The lower energy SGF (illustrated in FIG. 10A) was defined with s=128 and the higher energy SGF (illustrated in FIG. 10B) was defined with s=12.8 both with $N_s$=105. The higher energy SGF pulse had a $|\vec{E}|$ peak located in the occipital electrode of 580 V/m ($\angle 3.5\ 10^{-6}$ deg). The lower energy SGF pulse had a twofold decrease in the $|\vec{E}|$ peak of 207 V/m ($\angle 3.1\ 10^{-6}$ deg) also located in the occipital electrode. Both the higher and lower energy SGF pulses had null of $|\vec{E}|$ located in the central spinal canal.

The conductivity (dB relative to 1•) of all the tissues in the head at 500 kHz was approximately the same when computed using all three pulsing schemes: higher, lower and dual energy SGF. Conductivity had an unbounded upper limit (that is, Inf) in correspondence of the PEC material, where the electric field was null. Conductivity had null of σ located in the central spinal canal. The skin conductivity was 0.4 S/m and white and gray matter σ was 0.1 S/m. Muscle had a conductivity of 2 S/m, cerebral spinal fluid 13 S/m and bone 0.06 S/m.

Figure 11A:
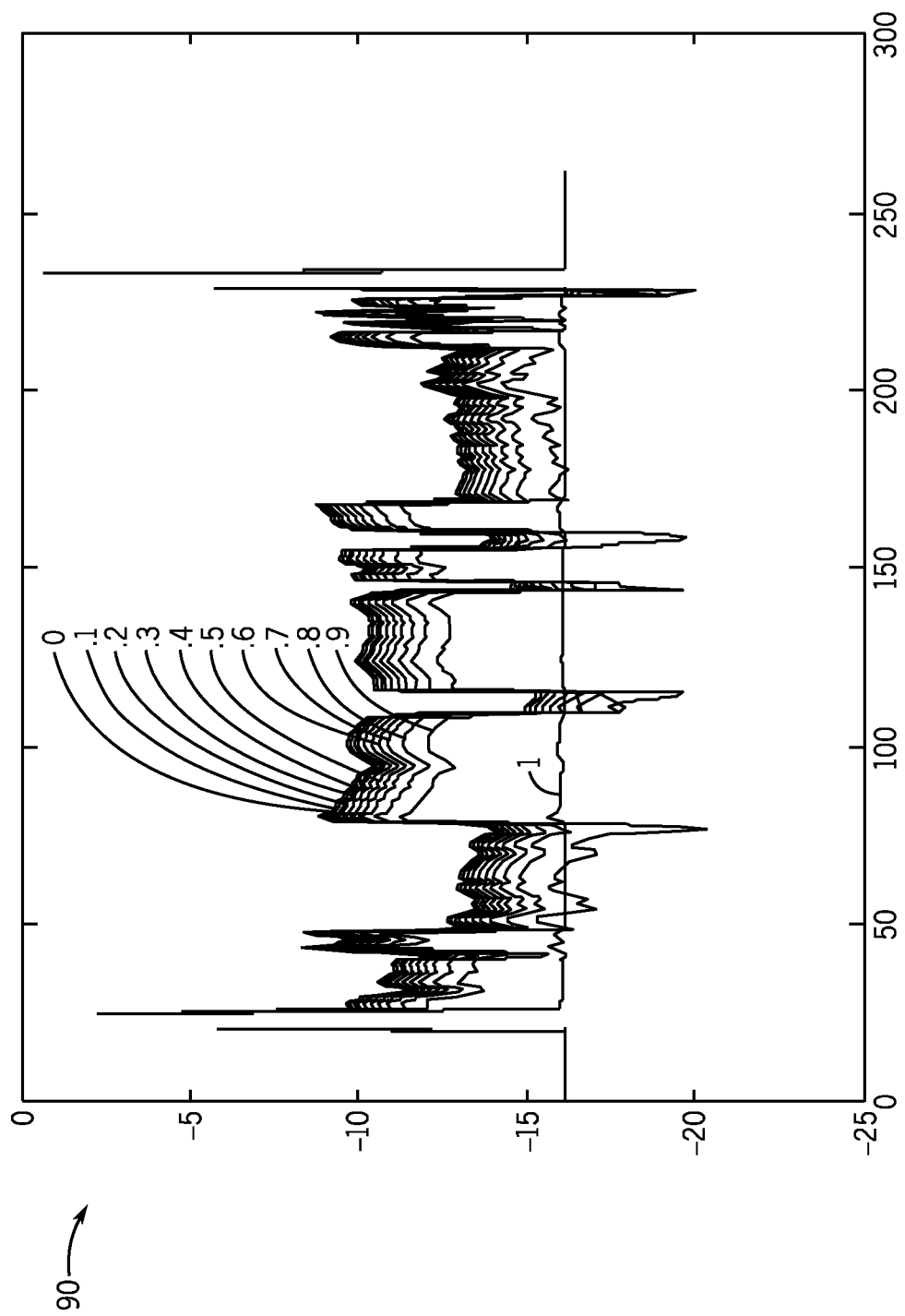
FIG. 11A is a simulation plot of current density magnitude as a function of posterior-to-anterior distance along the realistic head model.
Figure 11B:
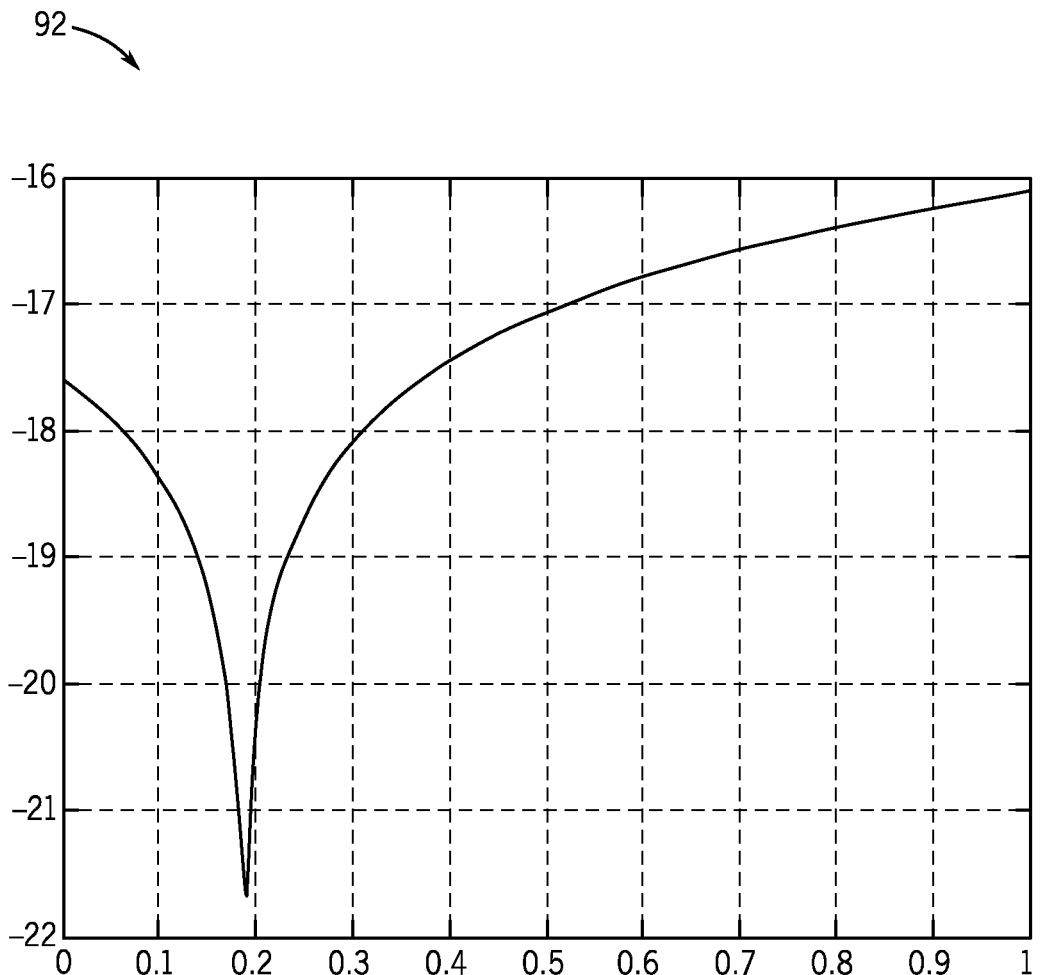
FIG. 11B is a simulation plot of current density magnitude as a function of frequency (w-values)

FIG. 11A is a graph 90 illustrating how the profile of the weighted current density magnitude in equation (12), (center slice in dB relative to 1 A/m2) as the weighting between the two SGF functions varies between w=0 and w=1. For the case w=1 (low energy), the current density in the skin peaks, whereas for the case w=0 (high energy), the current density in the center of the brain parenchyma peaks. The optimal weighting of w=0.2 is shown in the plot 92 of FIG. 11B, where at this value the amplitude of the current density on the skin is minimum compared to any other values of w.

FIGS. 12A-12C illustrate the magnitudes of the current density for cases of high energy 53 (FIG. 12A), low energy 55 (FIG. 12C), and dual energy 51 with w=0.2 (weighted subtraction, optimal value, FIG. 12B). In the case of w=0.2, there is maximal sensitivity to CSF and blood compared to the cases of high or low energy alone. The current density in high energy SGF peaked at 2.4 $10^4$ A/m² and low energy SGF peaked at 4.7 $10^3$ A/m² located both in the occipital electrode. All current densities magnitudes were null around the head model. Finally, the w=0.2 case had a current density amplitude near the electrode of 3.1 $10^{-6}$ A/m² or a reduction of approximately 3 million times compared to a single SGF stimulation pulse after normalization. The CSF is clearly the tissue that has the highest current density magnitude that peaks at 0.02 A/m².

The head model and FDTD simulations described above illustrate that the proposed SGF dual energy scheme results in improved sensitivity and specificity of EIS measurements of deep brain parenchymal impedance, compared to single stimulus methods. Unlike "absolute" and "simple linear" frequency difference imaging methods, which subtract two single sinusoidal sensing pulses at two different individual frequencies to calculate impedance, SGF dual energy subtraction makes no assumptions regarding the shape of the impedance distribution as a function of frequency, that is, in the dual energy method, all subtractions are performed in frequency without requiring any interpolation. In addition, generally, with regard to sampling strategies, sampling can be performed at the Nyquist rate. This method, however, does not optimize the number of samples, which can be obtained by following Landau's approach of signal demodulation followed by a lower sampling rate, where the demodulation is specifically implemented for the case of noise amplitude modulation. An alternative sampling approach that does not require demodulation can be achieved by periodically non-uniform sampling that results in an optimal average sampling period equal to the SGF's bandwidth.

In the above description, the modeling of each tissue was carefully performed based on the very accurate morphometry of the head model and known tissue dielectric constants. Most tissues in the human head have complex but well characterized anatomical features that were accurately reflected in our model (for example, cortical bone has a flat frequency response, but skull impedance varies due to other tissues present, such as fatty marrow). Despite this, there is clearly considerable inter-subject variability in the shape and composition of head structures, which represents a limitation of the current model. It may be possible, however, to control for these patient specific variables in future models by incorporating concurrent CT or MRI morphometric measurements. Impedance imaging methods such as Magnetic Resonance Electric Properties Tomography (MREPT) are also being developed which could further help refine future models.

From the above, it should be apparent that the SGF has a marked cylindrical shape in the time-frequency domain, produces steady values in frequency, and has a Gaussian shape in time. Furthermore, the SGF is a suitable model for electrical impedance spectroscopy pulses and facilitates greater penetrating depth than with previous EIS systems and methods. SGF-based pulses with different energies exhibit different penetration in the head and thus may be used to estimate more focused parenchymal tissue impedances. Thus, subtraction imaging may be achieved by combining the Gabor function with previous "white noise" pulse generation systems and methods (that is, "dual energy" imaging). Such dual energy systems and methods further facilitate portable, noninvasive detection and monitoring of stroke and intracranial hemorrhage.

The present inventors have demonstrated the feasibility of employing the present systems and methods to assess chronic stroke outpatients and neurological ICU patients with intracranial hemorrhage or ischemic stroke. The present EIS systems and methods have also been shown to be suitable for use with patients having acute/subacute subdural and epidural hematoma as well as more complex acute/subacute traumatic hemorrhagic lesions including small hematomas, traumatic hemorrhagic shear injury, and concussion associated with TBI.

The present EIS systems and methods facilitate portable "point-of-care" detection and characterization of acute brain injury as well as early detection through monitoring of hemorrhagic or edematous complications. These functionalities are not available with previous imaging systems or methods. Furthermore, portable EIS systems and methods can be advantageously employed not only in military and humanitarian assistance missions, but also more broadly for first responders, ambulances, and intensive care units (ICUs). Such systems and methods may not provide detailed anatomical imaging, but instead alert caregivers of an event in progress so that triage to more accurate imaging (such as CT and/or MRI) could be performed. That is, in some applications, the present systems and methods may lack sufficient diagnostic specificity to justify thrombolytic administration in the field; however, the present systems and methods provide knowledge of probable brain injury and facilitate appropriate triage/disposition of patients.

Thus, the present systems and methods may advantageously be used to monitor (1) patients admitted for inpatient or ICU monitoring (for example, in tertiary care hospitals with regional stroke centers, community hospitals, operating rooms, and other urgent care facilities) following stroke or other acute brain injury; (2) patients assessed in the field (for example, in ambulances, sports arenas, or battlefields) or in emergency departments (for example, in the facilities listed above) for signs and symptoms of stroke, hemorrhage, concussion, or other TBI; and (3) patients undergoing vascular invasive procedures (for example, in operating rooms of the facilities listed above) that place them at risk for stroke. The present systems and methods are advantageously non-invasive, accurate, affordable, portable, and capable of frequent or continuous operation.

In addition, such dual energy systems may also be utilized in short time spectral impedance measurements to capture events that occur in short time interval, for example for potential cardiac or respiratory monitoring applications. Given the properties of broadband and compactness, the SGF based spectral impedance estimations may be optimal for non-stationary measurements. Furthermore, optimization of depth sensitivity in EIS measurement using dual energy SGF excitation pulses has the potential to help develop proposed future point-of-care clinical applications, such as intracranial hemorrhage and stroke detection, as described above, as well as non-invasive assessment of radiation injury, cervical intraepithelial neoplasia, perinatal hypoxia, thyroid nodules classification, and functional electrical stimulation efficacy.

In light of the above, in one aspect, the present invention generally provides a system for determining brain health of a subject. The system includes a plurality of electrodes configured to be disposed proximate the head of the subject. A controller operatively connects to the plurality of electrodes, and the controller is configured to: (a) utilize a Stochastic Gabor Function to create an excitation pulse designed to be transmitted toward the brain of the subject by the plurality of electrodes; (b) acquire electrical impedance information from the brain of the subject in response to transmission of the excitation pulse; and (c) generate a report indicating a health of the brain of the subject from the electrical impedance information. The controller can be configured to compare the electrical impedance information to predetermined normal electrical impedance information prior to generating the report, and the report can include a current penetration depth image.

In another aspect, the present invention provides a system for determining brain health of a subject. The system includes a plurality of electrodes configured to be disposed proximate the head of the subject. A controller operatively connects to the plurality of electrodes, and the controller is configured to create a first excitation pulse and a second excitation pulse designed to be transmitted toward the brain of the subject by the plurality of electrodes. The controller utilizes a Stochastic Gabor Function to create the first excitation pulse, and the first and second excitation pulses are at different energies/frequencies and have different frequency shapes. The second excitation pulse is created by the Stochastic Gabor Function or created by a white noise generator of the controller. The controller is also configured to acquire electrical impedance information from the brain of the subject in response to transmission of the first excitation pulse and the second excitation pulse. The controller is further configured to generate a report indicating a health of the brain of the subject from the electrical impedance information.

In this system, the controller may be configured to compare the electrical impedance information to predetermined normal electrical impedance information prior to generating the report. In addition, the electrical impedance information can include first electrical impedance information acquired in response to transmission of the first excitation pulse, second electrical impedance information acquired in response to transmission of the second excitation pulse, and electrical impedance difference information obtained by subtracting the second electrical impedance information from the first electrical impedance information, and the report can indicate the health of the brain of the subject from the electrical impedance difference information.

Furthermore, in the above system the controller may be further configured to: create a first current penetration depth image in response to transmission of the first excitation pulse; create a second current penetration depth image in response to transmission of the second excitation pulse; and create a normalized difference image by subtracting features from the first current penetration depth image that are common to both the first current penetration depth image and the second current penetration depth image, and the report can include the normalized difference image.

In yet another aspect, the present invention provides a non-transitory computer-readable storage medium having software code stored therein that, when executed by a processor, causes the processor to perform analysis of brain health of a subject including the steps of: (a) directing a pulse generator operatively connected to the processor to create a first excitation pulse and a second excitation pulse designed to be transmitted toward the brain of the subject by a plurality of electrodes operatively connected to the pulse generator, the pulse generator utilizing a Stochastic Gabor Function to create the first excitation pulse, and the first and second excitation pulses being at different energies/frequencies and with different frequency shapes; (b) acquiring electrical impedance information from the brain of the subject in response to transmission of the first excitation pulse and the second excitation pulse; and (c) generating a report indicating a health of the brain of the subject from the electrical impedance information.

In addition, the processor can further perform the step of comparing the electrical impedance information to predetermined normal electrical impedance information prior to generating the report. The electrical impedance information can include first electrical impedance information acquired in response to transmission of the first excitation pulse, second electrical impedance information acquired in response to transmission of the second excitation pulse, and electrical impedance difference information obtained by subtracting the second electrical impedance information from the first electrical impedance information, and the report indicates the health of the brain of the subject from the electrical impedance difference information. Furthermore, the processor can further performs the steps of: creating a first current penetration depth image in response to transmission of the first excitation pulse; creating a second current penetration depth image in response to transmission of the second excitation pulse; and creating a normalized difference image by subtracting features from the first current penetration depth image that are common to both the first current penetration depth image and the second current penetration depth image, and the report can include the normalized difference image.

In yet another aspect, the present invention provides a method of determining brain health of a subject, comprising the steps of: (a) positioning a plurality of electrodes proximate the head of the subject; (b) creating a first excitation pulse by utilizing a Stochastic Gabor Function; (c) creating a second excitation pulse having a different energy/frequency and frequency shape than the first excitation pulse; (d) transmitting the first excitation pulse and the second excitation pulse toward the brain of the subject via the plurality of electrodes; (e) acquiring electrical impedance information from the brain of the subject in response to transmission of the first excitation pulse and the second excitation pulse; and (f) generating a report indicating a health of the brain of the subject from the electrical impedance information.

The method can further include the step of comparing the electrical impedance information to predetermined normal electrical impedance information prior to generating the report. In addition, the electrical impedance information can include first electrical impedance information acquired in response to transmission of the first excitation pulse, second electrical impedance information acquired in response to transmission of the second excitation pulse, and electrical impedance difference information obtained by subtracting the second electrical impedance information from the first electrical impedance information, and the report can indicate the health of the brain of the subject from the electrical impedance difference information. In addition, the method can include the steps of: creating a first current penetration depth image in response to transmission of the first excitation pulse; creating a second current penetration depth image in response to transmission of the second excitation pulse; and creating a normalized difference image by subtracting features from the first current penetration depth image that are common to both the first current penetration depth image and the second current penetration depth image, and the report can include the normalized difference image.

The various configurations presented above are merely examples and are in no way meant to limit the scope of this disclosure. Variations of the configurations described herein will be apparent to persons of ordinary skill in the art, such variations being within the intended scope of the present application. In particular, features from one or more of the above-described configurations may be selected to create alternative configurations comprised of a sub-combination of features that may not be explicitly described above. In addition, features from one or more of the above-described configurations may be selected and combined to create alternative configurations comprised of a combination of features which may not be explicitly described above. Features suitable for such combinations and sub-combinations would be readily apparent to persons skilled in the art upon review of the present application as a whole. The subject matter described herein and in the recited claims intends to cover and embrace all suitable changes in technology.

The invention claimed is:

1. A system for monitoring the brain of a subject, the system comprising:
   an electrical stimulator configured to apply a current to at least one pair of electrodes, the electrodes configured to be positioned on a skull of the subject to apply the current and to receive brain activity of the subject, wherein the electrical stimulator is configured to apply a current having a waveform according to a Stochastic Gabor Function (SGF), wherein the waveform includes a dual energy pulse;
   a signal processor configured to record the brain activity of the subject in the form of spectral electrical impedance data; and
   a computer system having non-transient computer readable media programmed and configured to process the spectral electrical impedance data and indicate an impedance change within the brain of the subject.

2. The system of claim 1 wherein a pulse of the dual energy pulse is formed of white noise.

3. The system of claim 2 wherein the computer readable media is programmed to subtract images of differing energies represented by the spectral electrical impedance data.

4. The system of claim 3 wherein the subtraction of the images is programmed to distinguish between ischemic and hemorrhagic stroke.

5. The system of claim 2 wherein the dual energy pulse provides impedance change within a depth of greater than about 1 mm in the brain.

6. The system of claim 1 wherein the current comprises white noise.

7. The system of claim 1 wherein the electrical stimulator is configured to apply current frequencies between about 10,000 kHz and 100,000 kHz.

8. The system of claim 1 wherein the electrical stimulator is configured to apply current frequencies between about 30,000 kHz and 500,000 kHz.

9. A method for monitoring the brain of a subject, the method comprising:
   positioning a plurality of electrodes on a skull of the subject;

applying a current to at least one pair of the electrodes, the current having a waveform based on a Stochastic Gabor Function (SGF), the waveform including a dual energy pulse;

measuring brain activity of the subject in the form of spectral electrical impedance data and storing the data within a non-transient computer readable media; and processing, using a computer system, the data so as to obtain an indication of an impedance change within the brain of the subject.

10. The method of claim 9 wherein a pulse of the dual energy pulse is formed of white noise.

11. The method of claim 10 wherein the impedance change is associated with the indication of stroke.

12. The method of claim 11 wherein the impedance change is associated with distinguishing the stroke between an ischemic and hemorragic stroke.

13. A system for analyzing a brain of a subject, comprising:

a plurality of electrodes configured to be coupled to the subject to deliver excitation pulses to a brain of the subject and receive electrical information from the brain of the subject, the excitation pulses including dual energy pulses;

a controller operatively connected to the plurality of electrodes, the controller being configured to:

(a) utilize a Stochastic Gabor Function to control delivery of at least one pulse of the dual energy pulses by the plurality of electrodes to the brain of the subject;

(b) determine electrical information received by the plurality of electrodes from the brain of the subject in response to the dual energy pulses to determine spectral electrical impedance information; and (c) generate a report indicating a status of the brain of the subject based on the spectral electrical impedance information.

14. The system of claim 13 wherein another pulse of the dual energy pulses is formed of white noise.

* * * * *

UNITED STATES PATENT AND TRADEMARK OFFICE
CERTIFICATE OF CORRECTION

PATENT NO.       : 9,820,669 B2
APPLICATION NO.  : 14/420148
DATED            : November 21, 2017
INVENTOR(S)      : Giorgio Bonmassar et al.

It is certified that error appears in the above-identified patent and that said Letters Patent is hereby corrected as shown below:

In the Specification

Column 13, Line 56, "1•" should be --1 $\Omega$--.

Signed and Sealed this
Eighth Day of May, 2018

Andrei Iancu
*Director of the United States Patent and Trademark Office*